(12) United States Patent
Kreutz

(10) Patent No.: US 6,395,720 B1
(45) Date of Patent: May 28, 2002

(54) SYNERGISTICALLY ACTING COMPOSITIONS FOR SELECTIVELY COMBATING TUMOR TISSUE

(76) Inventor: Werner Kreutz, Am Schlossberg D-79219, Staufen (DE)

( * ) Notice: Subject to any disclaimer, the term of this patent is extended or adjusted under 35 U.S.C. 154(b) by 0 days.

(21) Appl. No.: 09/446,570

(22) PCT Filed: May 19, 1998

(86) PCT No.: PCT/EP98/02939

§ 371 (c)(1),
(2), (4) Date: Mar. 27, 2000

(87) PCT Pub. No.: WO98/58639

PCT Pub. Date: Dec. 30, 1998

(30) Foreign Application Priority Data

Jun. 24, 1997 (DE) .......................... 197 26 871

(51) Int. Cl.$^7$ ................................................ A61K 31/60
(52) U.S. Cl. ...................................... 514/160; 514/165
(58) Field of Search .................................. 514/165, 160

(56) References Cited

U.S. PATENT DOCUMENTS 4,871,570 A 10/1989 Barnett et al. .............. 426/535
5,985,927 A * 11/1999 Kreutz ....................... 514/568

FOREIGN PATENT DOCUMENTS

WO          96 30003 A      10/1996

OTHER PUBLICATIONS

Derwent, Database XP–002076797, See Abstract.

* cited by examiner

*Primary Examiner*—Jerome D. Goldberg
(74) *Attorney, Agent, or Firm*—Anderson Kill & Olick; Eugene Lieberstein; Michael N. Meller

(57) ABSTRACT

According to the invention, compositions are made available which have a strong cytotoxic effect which is largely selective on tumor tissue. The invention is based on the fact that certain benzoic acid derivatives have a strong synergistic effect as a mixture and destroy cancer cells selectively in a pH range of 7 or below, such as from 6.5 to 7.

2 Claims, 3 Drawing Sheets

SYNERGISTICALLY ACTING COMPOSITIONS FOR SELECTIVELY COMBATING TUMOR TISSUE

The invention relates to novel synergistic compositions which selectively control tumor tissue, while healthy tissue is virtually unattacked. The novel compositions are therefore outstandingly suitable for cancer therapy.

Medicaments according to the prior art which are employed in chemotherapy as a rule only achieve partial success, i.e. they do not lead to a final cure. Moreover, the substances employed in the prior art frequently act only in a certain tumor category. A further disadvantage of the currently known chemotherapeutics are their often harmful side effects, as chemotherapeutics can generally have a cytostatic effect on proliferating tissue. The known chemotherapeutics are also unsatisfactory in the control of metastasis formation, and this is one of the main reasons which has until now prevented a decisive outcome in cancer therapy.

The fact that tumor tissue in an extracellular medium has a lowered average pH of about 6.5 to 7.0 and the pH can even fall to 5 on the cancer cell surface, while the pH in the normal tissue and in the blood is approximately 7.2 to 7.5, is known and described, for example, in DE-A 44 07 484 and in Tumor Biol., 1994, 15: 304–310. Thus each type of tumor has an intrinsic average intercellular pH, which, for example, in the case of breast tumors is about 6.7 and in the case of colon tumors about 6.9.

In the abovementioned publications, it is disclosed that due to the lowering of the pH range in tumor cells the natural immune defense is blocked, as the body's own defense cells react to cancer target cells with full cytotoxicity only in a slightly basic medium of pH more than 7. DE-A 44 07 484 therefore proposes to bring the acidic external medium of cancer cells to the normal physiological pH level of 7 to 7.5 and thereby to control the cancer cells by means of the body's own immune defense. For this purpose, the acidic external medium of cancer cells is brought to a physiological pH of 7 to 7.5 either by artificial basification measures or by the prevention of the acidification process itself.

The medicaments described in DE-A 44 07 484 admittedly represent an advance in cancer therapy, it would be desirable, however, to have available medicaments which besides the body's own immune defense selectively control tumor cells and thus can be used as relatively low-side-effect chemotherapeutics.

Accordingly, WO 96/30003 proposes to use those compounds for the control of tumor tissue which, at a pH of less than 7, are protonated or release a substance, the protonated compound or the released substance having a more strongly destructive effect on cells than the unprotonated compound or the compound before release of the substance. For these compounds, WO 96/30003 discloses general formulae under which come a multiplicity of chemical compounds. Inter alia, 4-amino-2-hydroxybenzoic acid is mentioned as being effective there. Acetylsalicylic acid is also mentioned as a possible active compound, but this compound is not preferred.

The compounds of WO 96/30003 and also the mixtures generally proposed there of two and more compounds admittedly do already have a good anti-tumor effect, but, as before, there is a need for medicaments which have an improved anti-tumor effect, in particular at pH values of 7.0 or below, in particular in the range from 6.5 to 7.0.

It is therefore an object of the present invention to make available novel medicaments which have a strong cytotoxic effect which is largely selective on tumor tissue, in particular in a pH range from approximately 6.5 to approximately 7.0.

This object is solved by the subject of the patent claims.

The compositions according to the invention in principle act in the same manner as the benzoic acid derivatives disclosed in WO 96/30003. It has been shown, however, that these benzoic acid derivatives, which are known from WO 96/30003, do not have completely satisfactory activity against tumor tissue. Surprisingly, however, individual benzoic acid derivatives as a mixture with one another have a very strongly synergistic action for the destruction of tumor tissue and in a pH range of approximately 7.0 and below cause a virtually complete cell death in tumor tissue.

The compositions according to the invention are mixtures which contain at least two of the following benzoic acid derivatives or cinnamic acid derivatives, respectively, which act synergistically as a mixture with one another:
2-acetoxybenzoic acid (acetylsalicylic acid, Aspirin®)
2-hydroxybenzoic acid
2-methoxybenzoic acid
2,4-dihydroxybenzoic acid
2,4-diacetoxybenzoic acid
2-hydroxy-4-aminobenzoic acid
2,4-dimethoxybenzoic acid
2,6-dihydroxybenzoic acid
2,6-dimethoxybenzoic acid
2,3,4-trimethoxybenzoic acid
2,4,6-trihydroxybenzoic acid
2,4,6-trimethoxybenzoic acid
5-(2,4-difluoro-phenyl)salicylic acid
α-cyano-3-hydroxycinnamic acid
α-cyano-4-hydroxycinnamic acid
α-fluorocinnamic acid
α-methylcinnamic acid and
α-acetamidocinnamic acid.

Preferably, the mixture contains at least two of the following benzoic acid derivatives, which act synergistically as a mixture with one another:
2-acetoxybenzoic acid (acetylsalicylic acid, Aspirin®)
2-methoxybenzoic acid
2,4-diacetoxybenzoic acid
2-hydroxy-4-aminobenzoic acid
2,4-dimethoxybenzoic acid
2,6-dihydroxybenzoic acid
2,6-dimethoxybenzoic acid
2,3,4-trimethoxybenzoic acid
2,4,6-trihydroxybenzoic acid and
2,4,6-trimethoxybenzoic acid These compounds are known as such, commercially available and can be prepared by a person skilled in the art without problems. They show their particular therapeutic benefits, however, only in the compositions according to the invention.

A synergistic effect is not seen with all mixtures of the abovementioned benzoic acid derivatives. Whether a synergistic action may be present in a mixture can be easily determined by a person skilled in the art taking into account the details below.

Synergistic compositions are, for example, the following mixtures:
2,6-dihydroxybenzoic acid/2-hydroxy-4-aminobenzoic acid
2,6-dihydroxybenzoic acid/acetylsalicylic acid
2,6-dihydroxybenzoic acid/2,4-diacetoxybenzoic acid
2,6-dihydroxybenzoic acid/2,4-dimethoxybenzoic acid
2-hydroxy-4-aminobenzoic acid/acetylsalicylic acid
2-hydroxy-4-aminobenzoic acid/2,4-dimethoxybenzoic acid and
2,4-dimethoxybenzoic acid/2-acetoxybenzoic acid.

Furthermore, the following mixtures can also be mentioned:

2,4,6-trihydroxybenzoic acid/2,4-dimethoxybenzoic acid
2,4,6-trihydroxybenzoic acid/2,6-dihydroxybenzoic acid
2,4,6-trimethoxybenzoic acid/2,6-dihydroxybenzoic acid
2,4,6-trimethoxybenzoic acid/2-hydroxy-4-aminobenzoic acid
2,4,6-trimethoxybenzoic acid/2,4,6-trihydroxybenzoic acid
2,4,6-trimethoxybenzoic acid/2,4-dimethoxybenzoic acid.

As further mixtures can also be mentioned:
2-hydroxy-4-aminobenzoic acid/5-(2,4-difluorophenyl) salicylic acid
2-acetoxybenzoic acid/5-(2,4-difluorophenyl)salicylic acid
2-acetoxybenzoic acid/α-cyano-3-hydroxycinnamic acid
5-(2,4-difluorophenyl)salicylic acid/α-cyano-3-hydroxycinnamic acid and
2-hydroxy-4-aminobenzoic acid/α-cyano-3-hydroxycinnamic acid.

The use of triple combinations of the mixtures is also especially preferred, whereby the following triple combinations have advantageous synergistic properties:
2-hydroxy-4-aminobenzoic acid/2-acetoxybenzoic acid/5-(2,4-difluorophenyl)salicylic acid
2-hydroxy-4-aminobenzoic acid/2-acetoxybenzoic acid/α-cyano-3-hydroxycinnamic acid
2-hydroxy-4-aminobenzoic acid/5-(2,4-difluorophenyl) salicylic acid/α-cyano-3-hydroxycinnamic acid and
2-acetoxybenzoic acid/5-(2,4-difluorophenyl)salicylic acid/α-cyano-3-hydroxycinnamic acid.

In the abovementioned mixtures 2-hydroxybenzoic acid (salicylic acid) can also be used instead of acetylsalicylic acid.

An example which may be mentioned of a nonsynergistic composition of the above constituents is a mixture of 2,4-diacetoxybenzoic acid and 2-hydroxy-4-aminobenzoic acid.

On account of their pH sensitivity, the compositions according to the invention are only activated in cancer tumors and metastatic areas and therefore represent an ideal cancer therapeutic. It is also to be particularly emphasized that this novel cancer therapeutic acts generally on all tumor types independently of the specific type of cancer.

It is assumed that the substance mixtures according to the invention have toxic properties in the protonated state and act as cellular toxins on the tumors.

It is known that the pHs in the extracellular tumor tissue can be lowered again by about 0.5 pH units by inducing acidosis by glucose administration. Such an administration of glucose can likewise take place with the compositions according to the invention.

The compositions according to the invention can contain the active compounds in any desired proportions provided that the synergistic effect still occurs. How the activity of compounds and thus also the presence of a synergistic effect can be detected is described in detail, for example, in WO 96/30003, and in this respect reference can be made to this publication. Reference is further made to the following comparison examples.

The compositions according to the invention preferably contain the two active compounds in the ratio 1:9 to 9:1, particularly preferably in the ratio 2:1 to 1:2 and in particular in the ratio of approximately 1:1.

The synergistic activity of the compositions according to the invention was clearly confirmed by in vitro experiments. In the following, the following short forms are used for the following substance names:

Substance 121 = acetylsalicylic acid (2-acetoxybenzoic acid)
Substance 58a = 2-hydroxy-4-aminobenzoic acid
Substance 132 = 2,4-diacetoxybenzoic acid
Substance 136 = 2,6-dihydroxybenzoic acid
Substance 188 = 2,4-dimethoxybenzoic acid The experiments according to the invention were carried out as follows:

The measurements were carried out using a "Cell Death Detection ELISA" kit, Cat. No. 1774 425 commercially available from Boehringer (Mannheim). The process instructions are additionally supplied by Boehringer.

The results can be seen from Tables 1 to 3 below. The OD value corresponds to the cell death.

TABLE 1

(Photometric measurement after 35 minutes)

| Compound | Initial pH | OD (405–490 nm) |
|---|---|---|
| CAM (800 ng/ml) | pH 6.0 | 0.818 |
|  | pH 6.5 | 3.037 |
|  | pH 7.0 | 2.725 |
|  | pH 7.4 | 2.416 |
| 136 (5 mM) | pH 6.0 | 0.187 |
|  | pH 6.5 | 0.918 |
|  | pH 7.0 | 0.321 |
|  | pH 7.4 | 0.382 |
| 136 (7 mM) | pH 6.0 | 0.221 |
|  | pH 6.5 | 1.287 |
|  | pH 7.0 | 0.524 |
|  | pH 7.4 | 0.816 |
| Negative control | pH 6.0 | 0.642 |
|  | pH 6.5 | 0.702 |
|  | pH 7.0 | 0.293 |
|  | pH 7.4 | 0.268 |
| Positive control |  | 3.145 |

TABLE 2

(Photometric measurement after 35 minutes)

| Compound | Initial pH | OD (405–490 nm) |
|---|---|---|
| CAM (160 ng/ml) | pH 6.0 | 0.344 |
|  | pH 6.5 | 0.711 |
|  | pH 7.0 | 1.220 |
|  | pH 7.4 | 1.923 |
| 58a (15 mM) | pH 6.0 | 0.320 |
|  | pH 6.5 | 0.282 |
|  | pH 7.0 | 0.574 |
|  | pH 7.4 | 1.835 |
| 121 (10 mM) | pH 6.0 | 1.282 |
|  | pH 6.5 | 0.163 |
|  | pH 7.0 | 0.413 |
|  | pH 7.4 | 1.508 |
| 132 (10 mM) | pH 6.0 | 2.856 |
|  | pH 6.5 | 0.183 |
|  | pH 7.0 | 0.088 |
|  | pH 7.4 | 0.502 |
| 188 (15 mM) | pH 6.0 | 0.256 |
|  | pH 6.5 | 0.309 |
|  | pH 7.0 | 0.502 |
|  | pH 7.4 | 1.854 |
| Negative control | pH 6.0 | 0.674 |
|  | pH 6.5 | 0.648 |
|  | pH 7.0 | 0.327 |
|  | pH 7.4 | 0.322 |
| Positive control |  | 1.940 |

TABLE 3

(Photometric measurement after 20 minutes)

| Compound | Initial pH | OD (405–490 nm) |
|---|---|---|
| CAM (800 ng/ml) | pH 6.0 | 1.681 |
| | pH 6.5 | 1.708 |
| | pH 7.0 | 1.791 |
| | pH 7.4 | 2.217 |
| 136 + 58a | pH 6.0 | 0.206 |
| (5 mM/10 mM) | pH 6.5 | 0.745 |
| | pH 7.0 | 2.036 |
| | pH 7.4 | 0.793 |
| 136 + 121 | pH 6.0 | 0.750 |
| (5 mM/5 mM) | pH 6.5 | 0.486 |
| | pH 7.0 | 2.564 |
| | pH 7.4 | 0.970 |
| 136 + 132 | pH 6.0 | 0.419 |
| (5 mM/5 mM) | pH 6.5 | 0.328 |
| 1st experiment | pH 7.0 | 0.802 |
| | pH 7.4 | 0.953 |
| 136 + 132 | pH 6.0 | 0.640 |
| (5 mM/5 mM) | pH 6.5 | 0.274 |
| 2nd experiment | pH 7.0 | 1.160 |
| | pH 7.4 | 1.124 |
| 136 + 188 | pH 6.0 | 0.211 |
| (5 mM/10 mM) | pH 6.5 | 1.728 |
| | pH 7.0 | 1.426 |
| | pH 7.4 | 0.804 |
| 58a + 121 | pH 6.0 | 0.577 |
| (10 mM/5 mM) | pH 6.5 | 0.480 |
| | pH 7.0 | 2.227 |
| | pH 7.4 | 1.238 |
| 58a + 132 | pH 6.0 | 0.152 |
| (10 mM/5 mM) | pH 6.5 | 0.241 |
| | pH 7.0 | 0.417 |
| | pH 7.4 | 1.082 |
| 58a + 188 | pH 6.0 | 0.251 |
| (10 mM/5 mM) | pH 6.5 | 1.698 |
| | pH 7.0 | 2.939 |
| | pH 7.4 | 0.915 |
| 132 | pH 6.0 | 0.407 |
| (5 mM) | pH 6.5 | 0.371 |
| | pH 7.0 | 0.422 |
| | pH 7.4 | 0.916 |
| Negative control | pH 6.0 | 0.883 |
| | pH 6.5 | 0.794 |
| | pH 7.0 | 0.330 |
| | pH 7.4 | 0.579 |
| Positive control | | 1.219 |

The results of the experiments are summarized in FIGS. 1 to 3, which correspond to Tables 1 to 3. In the figures, the cell death is recorded in a ELISA (apoptosis kit) with RT112 as a function of the pH. That is to say the data on the Y axis of the figures is a measure of the cell death; the pH of the cells is indicated on the X axis.

Figure 1:
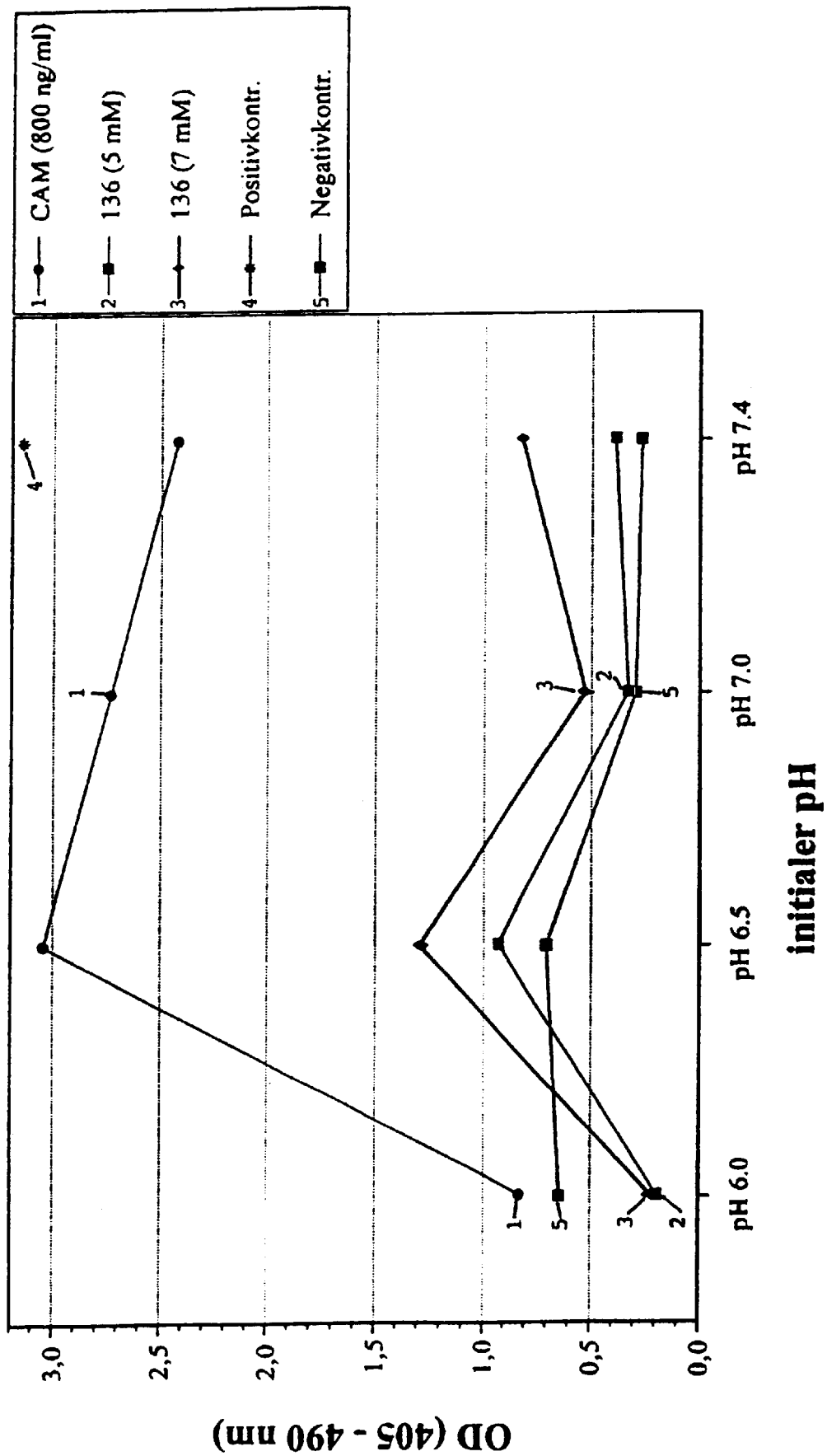
FIG. 1 and FIG. 2 show experiments in which individual compounds were employed.
Figure 2:
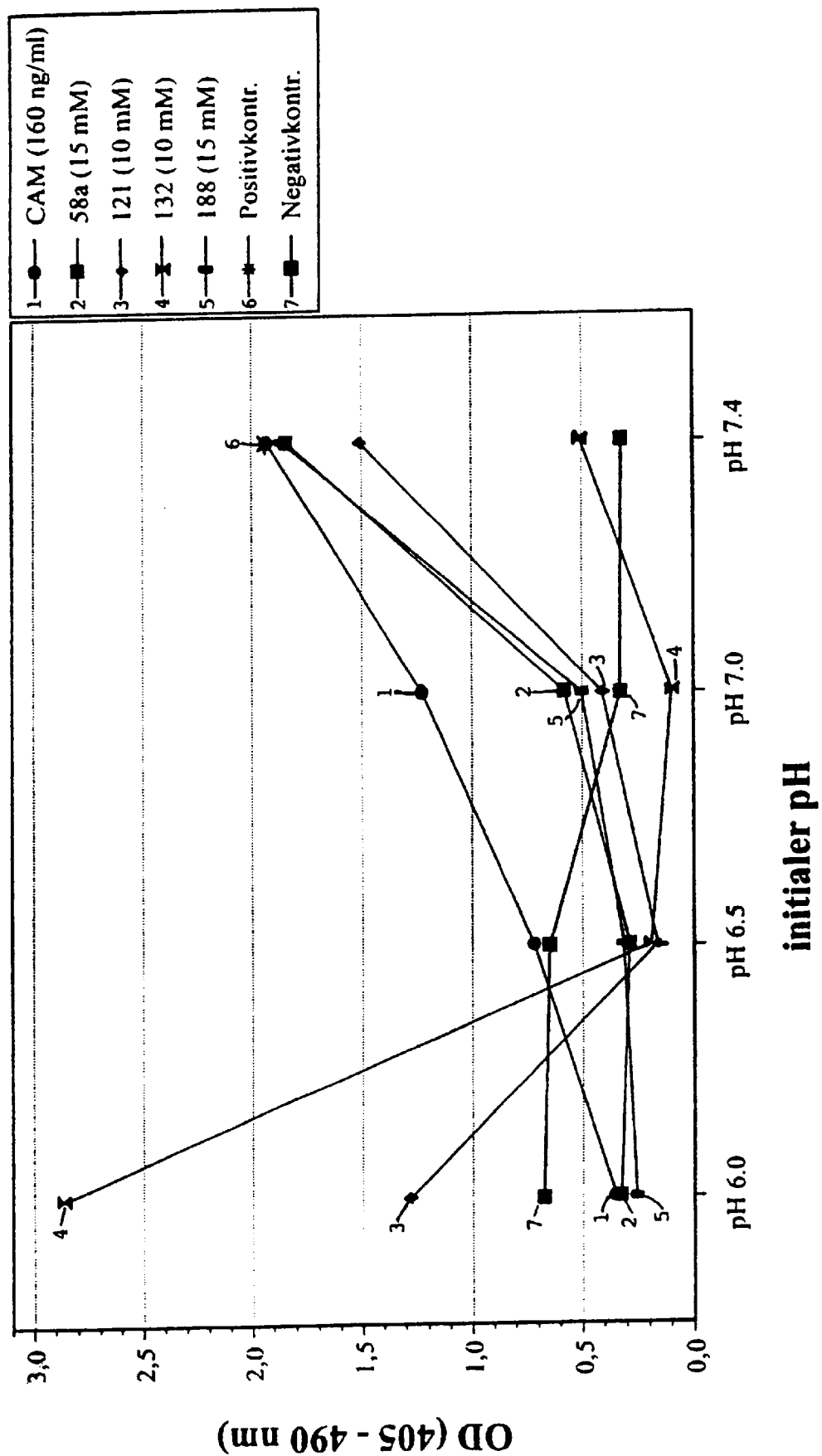
Figure 3:
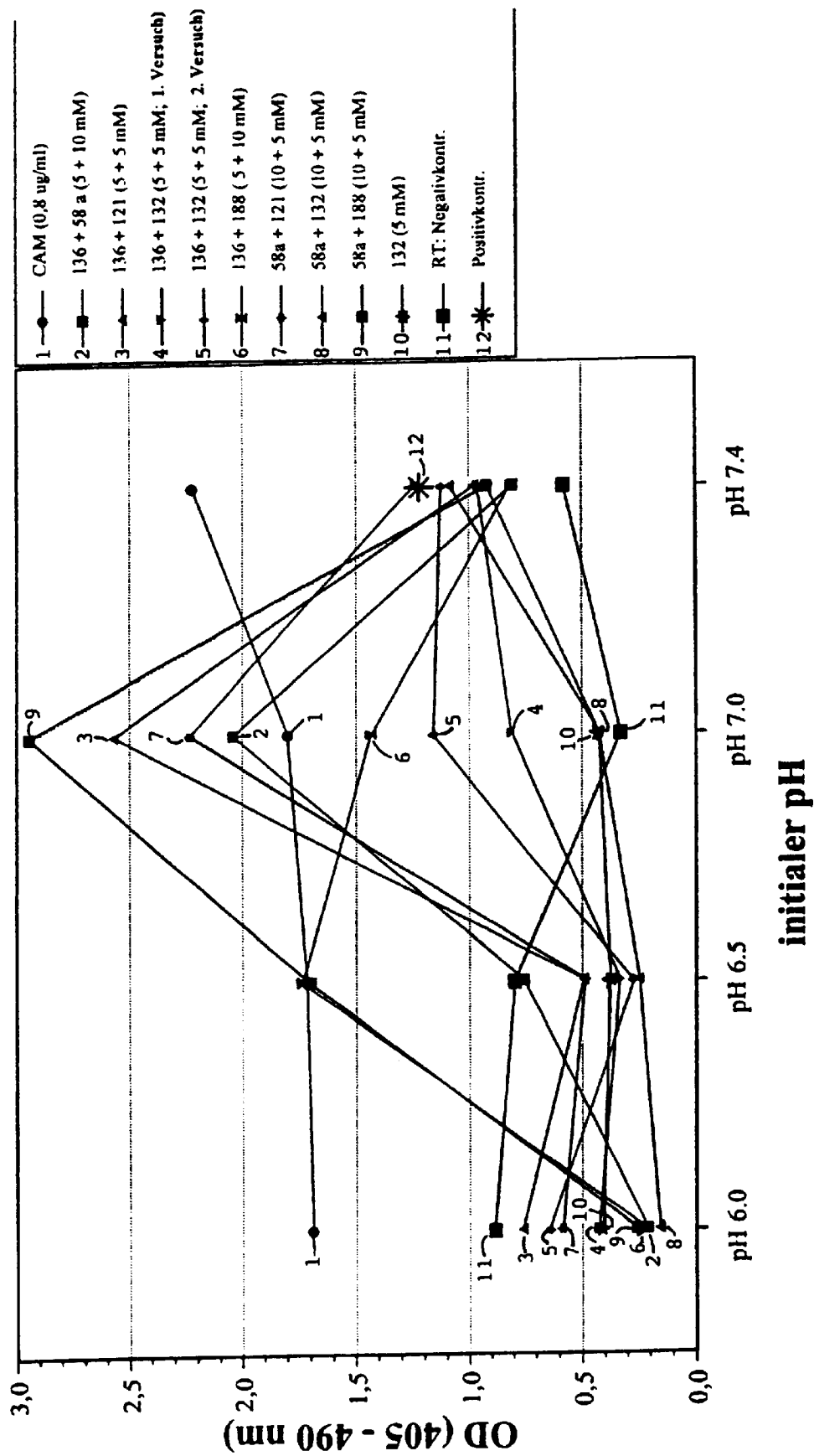
FIG. 3 shows the synergistic effect of the compositions according to the invention compared with the individual compounds. It stands out that at a pH of between 6.5 and 7.0 the compositions according to the invention cause a cell death which is preferably in the vicinity of or above the CAM value, which virtually corresponds to a complete destruction of the tumor tissue.

The apoptosis-inducing substance CAM used in the experiments is camptothecin (CAM value). In the experiments, positive control means that instead of the apoptotic cancer cells induced by the substances a histone-DNA complex with known detection sensitivity is employed for detection, i.e. an artificial apoptosis product is provided.

In the experiments, negative control means that the same detection procedure is carried out, but without addition of substances or substance mixtures.

From the comparison experiments it is obvious that certain mixtures of the abovementioned benzoic acid derivatives have a synergistic effect. The mixture of 2,4-diacetoxybenzoic acid and 2-hydroxy-4-aminobenzoic acid does not show any synergistic effect, and the ability of the mixture to destroy tumor cells is not higher than that of individual compounds in the example of 2,4-diacetoxybenzoic acid.

The compositions according to the invention can be formulated in a known manner for medicaments for mammals, preferably man. In the medicaments, the compositions according to the invention are present as a mixture with a pharmaceutical organic or inorganic excipient, which is suitable for enteral or parenteral administrations. The oral administration of the compositions according to the invention by means of tablets, capsules, powders or in liquid form, such as suspensions, in solution, as an emulsion or as a syrup, is particularly preferred.

In the case of formulation as tablets, customary pharmaceutical excipients such as sodium citrate, lactose, microcrystalline cellulose and starch, lubricants such as anhydrous silicic acid, hydrogenated castor oil, magnesium stearate, sodium lauryl sulfate and talc, as well as binders such as starch paste, glucose, lactose, gum arabic, mannitol, magnesium trisilicate and talc are used. If the compositions according to the invention are to be administered by means of liquids, customary liquid excipients can be used.

A formulation for injections and infusions is likewise preferred, as is known in the field and described in relevant standard works.

The compositions according to the invention can likewise be formulated in a manner known per se as depot formulations or to give medicaments having delayed or sustained release.

The dosage form of the compositions according to the invention depends on the specific composition and further factors and can be determined by a person skilled in the art on the basis of the condition of the patient to be treated, the severity and type of the disease to be treated, possible side effects of the substance mixtures administered, etc.

The dosage of the compositions according to the invention can be determined by a person skilled in the art depending on the specific disease, the patient and other circumstances and is, for example, 50 mg/kg of body weight up to 300 mg/kg of body weight, preferably 100 mg/kg of body weight up to 200 mg/kg of body weight, of the composition according to the invention per day.

It is obvious to the person skilled in the art that the compounds of the compositions according to the invention can be administered together or in succession at short time intervals such that they still have their synergistic effect. According to the invention, both the simultaneous administration of a suitably formulated substance mixture and the time-shifted or simultaneous administration of the suitably formulated individual constituents of the compositions according to the invention are included, provided that the time intervals between the administration of the individual constituents are not so large that the synergistic effect is lost.

The time interval between the administration of the individually formulated components is generally not more than 24 hours, preferably not more than one hour. Especially preferred is the joined administration of the formulations or the administration of one formulation immediately after the other.

Therefore, the invention also relates to a pharmaceutical pack consisting of two medicaments each of which contains at least one benzoic acid derivative selected from
2-acetoxybenzoic acid (acetylsalicylic acid, Aspirin®)
2-hydroxybenzoic acid
2-methoxybenzoic acid
2,4-dihydroxybenzoic acid
2,4-diacetoxybenzoic acid
2-hydroxy-4-aminobenzoic acid
2,4-dimethoxybenzoic acid
2,6-dihydroxybenzoic acid
2,6-dimethoxybenzoic acid
2,3,4-trimethoxybenzoic acid
2,4,6-trihydroxybenzoic acid
2,4,6-trimethoxybenzoic acid
5-(2,4-difluoro-phenyl)salicylic acid
α-cyano-3-hydroxycinnamic acid
α-cyano-4-hydroxycinnamic acid
α-fluorocinnamic acid
α-methylcinnamic acid and
α-acetamidocinnamic acid.
and, if applicable, a pharmaceutically acceptable carrier or thinner for the joined or timely shifted administration, whereby the pharmaceutical pack contains at least two different benzoic acid derivatives.

The preferred combinations of active agents of the pharmaceutical packs correspond to the abovementioned preferred mixtures of the invention.

Pharmaceutical pack can also be defined as the hint, for example on the package insert of a benzoic acid containing preparation, that this benzoic acid containing preparation should be administered jointly or timely shifted with another benzoic acid containing preparation. As a result, the invention also relates to a pharmaceutical pack as defined above, which is characterized in that the two medicaments are each provided in a separate package, whereby on one package insert of at least one of the packages it is pointed to the joined or timely shifted administration with the other medicament.

The following galenic example illustrates the invention and is not limiting.

EXAMPLE

A solution of 2-hydroxy-4-aminobenzoic acid in distilled water is prepared, whereby the concentration of the 2-hydroxy-4-aminobenzoic acid is selected in a way that the prepared solution is from isotonic (34 mg/ml 2-hydroxy-4-aminobenzoic acid) to slightly hypertonic (48 mg/ml 2-hydroxy-4-aminobenzoic acid), sterile and pyrogene free. Parallel thereto, a solution of 2-acetoxybenzoic acid obtainable under the tradename Aspisol is provided. Both solutions are administered to a patient intravenously one after the other, whereby the 2-hydroxy-4-aminobenzoic acid is administered in a dosage of 300 mg/kg body weight and the 2-acetoxybenzoic acid is administered in a dosage of 50 mg/kg body weight.

What is claimed is:

1. A method of treating carcinomatous disorders, comprising administrating to a patient in need thereof a pharmaceutically effective amount of a synergistic combination of 2-hydroxy-4-aminobenzoic acid and acetylsalicylic acid.

2. A synergistic combination for treating carcinomatous disorders comprising 2-hydroxy-4-aminobenzoic acid and acetylsalicyclic acid in an effective amount.

* * * * *